(12) United States Patent
Kyal et al.

(10) Patent No.: US 9,036,877 B2
(45) Date of Patent: May 19, 2015

(54) CONTINUOUS CARDIAC PULSE RATE ESTIMATION FROM MULTI-CHANNEL SOURCE VIDEO DATA WITH MID-POINT STITCHING

(71) Applicant: Xerox Corporation, Norwalk, CT (US)

(72) Inventors: Survi Kyal, Rochester, NY (US); Lalit Keshav Mestha, Fairport, NY (US); Beilei Xu, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 236 days.

(21) Appl. No.: 13/871,728

(22) Filed: Apr. 26, 2013

(65) Prior Publication Data

US 2013/0342670 A1    Dec. 26, 2013

Related U.S. Application Data

(63) Continuation-in-part of application No. 13/528,307, filed on Jun. 20, 2012, now Pat. No. 8,855,384.

(51) Int. Cl.
*G06K 9/00* (2006.01)
*A61B 5/00* (2006.01)
*A61B 5/024* (2006.01)

(52) U.S. Cl.
CPC ..... *A61B 5/7225* (2013.01); *G06T 2207/30004* (2013.01); *G06T 2207/30076* (2013.01); *G06K 9/00496* (2013.01); *A61B 5/7203* (2013.01); *A61B 5/0013* (2013.01); *A61B 5/0077* (2013.01); *A61B 5/02416* (2013.01); *A61B 5/7278* (2013.01)

(58) Field of Classification Search
CPC ........... G06T 2207/30076; G06T 2207/30004; G06K 9/00496; A61B 5/00

USPC .................................................. 382/107, 128
See application file for complete search history.

(56) References Cited

U.S. PATENT DOCUMENTS

| 6,934,578 | B2 * | 8/2005 | Ramseth | 600/523 |
| 2003/0161527 | A1 * | 8/2003 | Wang | 382/156 |
| 2009/0072824 | A1 * | 3/2009 | Romero | 324/303 |

(Continued)

OTHER PUBLICATIONS

Wei Lu et al., "Approach and Applications of Constrained ICA", IEEE Transactions on Neural Networks, vol. 16, No. 1, Jan. 2005.

(Continued)

*Primary Examiner* — Utpal Shah
(74) *Attorney, Agent, or Firm* — Philip E. Blair; Fleit Gibbons Gutman Bongini & Bianco P.L.

(57) ABSTRACT

What is disclosed is a novel system and method for extracting photoplethysmographic (PPG) signals (i.e., cardiac signals) on a continuous basis from signals generated from video images captured of a subject being monitored for cardiac function in a non-contact remote sensing environment. In one embodiment, a time-series signal is received. The time-series signal is generated from video images captured of a region of exposed skin where a PPG signal of a subject of interest can be registered. The time-series signal is then divided into batches for processing, with successive batches having at least a 95% overlap with a previous batch. Each of the batches of time-series signals is processed to obtain a PPG signal from each batch. A mid-point of each of these PPG-signals is stitched together to obtain a continuous PPG signal for the subject. The continuous PPG signal for the subject can then viewed on a display device.

25 Claims, 13 Drawing Sheets

(56) References Cited

U.S. PATENT DOCUMENTS

| | | | |
|---|---|---|---|
| 2011/0251493 A1 | 10/2011 | Poh et al. | |
| 2013/0226858 A1* | 8/2013 | Smaragdis et al. | 706/52 |
| 2013/0290011 A1* | 10/2013 | Lynn et al. | 705/2 |
| 2013/0296660 A1* | 11/2013 | Tsien et al. | 600/301 |

OTHER PUBLICATIONS

Wei Lu et al., "Constrained Independent Component Analysis", School of Computer Engineering, Nanyang Technological University, Singapore 639798, 2001.

Takano et al., "Heart rate measurement based on a time-lapse image", Medical Engineering & Physics 29 (2007), pp. 853-857, www.sciencedirect.com.

Poh et al., "Non-contact, automated cardiac pulse measurements using video imaging and blind source separation.", May 10, 2010, vol. 18, No. 10 / Optics Express 10762.

Lee et al., "Temporally constrained ICA-based foetal ECG separation", Electronics Letters, Oct. 13, 2005, vol. 41, No. 21.

Mestha et al., "Systems and Methods for Non-Contact Heart Rate Sensing", U.S. Appl. No. 13/247,575, filed Sep. 28, 2011.

Xu et al., "A Multi-Layer Array for a Multi-Resolution Multi-Spectral Camera," U.S. Appl. No. 13/239,642, filed Sep. 22, 2011.

Yang et al., "Vital Sign Estimation from Passive Thermal Video," IEEE Conference on Computer Vision and Pattern Recognition, Jun. 2008, pp. 23-28.

Garbey et al., "Contact-Free Measurement of Cardiac Pulse Based on the Analysis of Thermal Imagery," Department of Computer Science, University of Houston, Dec. 14, 2004.

Mestha et al., "Method for Classifying a Pixel of a Hyperspectral Image in a Remote Sensing Application," U.S. Appl. No. 13/023,310, filed Feb. 8, 2011.

Wang et al., "Determining a Total Number of People in a IR Image Obtained Via an IR Imaging System," U.S. Appl. No. 12/967,775, filed Dec. 14, 2010.

Xu et al., "System and Method for Object Identification and Tracking," U.S. Appl. No. 13/247,343, filed Sep. 28, 2011.

Lee et al., "Speech Coding and Noise Reduction Using ICA-Based Speech Features," in P. Pajunen and J. Karhunen (eds.), Proc. Second International Workshop on Independent Component and Analysis and Blind Signal Separation, 2000.

Hoyer et al., "ICA Features of Colour and Stereo Images," P. Pajunen and J. Karhunen (eds.), Proc. Second International Workshop on Independent Component and Analysis and Blind Signal Separation, 2000, pp. 567-572.

Bell et al., "The "Independent Components" of Natural Science are Edge Filters," Vision Ref., 1997, vol. 37, No. 23, pp. 3327-3338.

Lee et al., "Application of independent component analysis to microarrays," Genome Biology, 2003, vol. 4, Issue 11, R76.

Cantelli, Mark, "Are you in There?" Tolltrans 2011, www.TrafficTechnologyToday.com.

Mestha, et al., "Estimating Cardiac Pulse Recovery From Multi-Channel Source Data Via Constrained Source Separation", U.S. Appl. No. 13/247,683, filed Sep. 28, 2011.

Mestha et al., "Filtering Source Video Data Via Independent Component Selection", U.S. Appl. No. 13/281,975, filed Nov. 8, 2011.

Cardoso, Jean-Francois, "Blind signal separation: statistical principles", pp. 1-16, (Official Version published as: Proceedings of the IEEE, vol. 9, No. 10, pp. 2009-2025, Oct. 1998).

Hyvarinen et al., "Independent Component Analysis: Algorithms and Applications", Neural Networks Research Centre, Helsinki University of Technology, Finland, Neutral Networks, pp. 1-31, 13(4-5); 411-430, 2000.

Wang et al., "Determining a Number of Objects in an IR Image", U.S. Appl. No. 13/086,006, filed Apr. 28, 2011.

Wang, et al., "Post-Processing a Multi-Spectral Image for Enhanced Object Identification", U.S. Appl. No. 13/324,368, filed Dec. 28, 2011.

Mestha et al., "Removing Environment Factors From Video Signals Captured for Biomedical Measurements", U.S. Appl. No. 13/401,207, filed Feb. 21, 2012.

Pressman et al., "A Transducer for the Continuous External Measurement of Arterial Blood Pressure", External Measurement of Blood Pressure, IEEE Transactions on Bio-Medical Electronics, Apr. 1963, pp. 73-81.

Meigas et al., "Continuous Blood Pressure Monitoring Using Pulse Wave Delay", Proposed Paper; Engineering in Medicine and Biology Society, 2001, vol. 4, pp. 3171-3174, Proceedings of the 23rd Annual Int'l Conf. of the IEEE.

Penaz, J., "Photoelectric Measurement of Blood Pressure, Volume and Flow in the Finger", Dresden, 10th Int. Conf. Med. and Biol. Engineering, 1973, Session 7, N2, Haemodynamics I, pp. 161-164.

Aubert et al., "A Model-Based Study of the Influence of Vaso-Active Drugs on Pulse Delays Measured from the Electrocardiogram", Computers in Cardiology 2007:34:383-386.

Naschitz et al., "Pulse Transit Time by R-Wave-Gated Infrared Photoplethysmography: Review of the Literature and Personal Experience", Journal of Clinical Monitoring and Computing (2004) 18: 333-342, Springer 2005.

Reisner et al., "Utility of the Photoplethysmogram in Circulatory Monitoring", Anesthesiology, vol. 108, No. 5, May 2008, pp. 950-958.

Dalal et al., "Histograms of Oriented Gradients for Human Detection", Proceedings of the Conference on Computer Vision and Pattern Recognition, San Diego, California, USA, pp. 886-893, (2005).

Skaff et al., "Estimating a Visible Vector Representation for Pixels in an Infrared Image", U.S. Appl. No. 13/364,835, filed Feb. 2, 2012.

Xu et al., "Subcutaneous Vein Pattern Detection Via Multi-Spectral IR Imaging in an Identity Verification System", U.S. Appl. No. 13/087,850, filed Apr. 15, 2011.

Mestha et al., "Deriving Arterial Pulse Transit Time From a Source Video Image", U.S. Appl. No. 13/401,286, filed Feb. 21, 2012.

Piratla et al., "Web-Based System and Method for Video Analysis", U.S. Appl. No. 13/417,979, filed Mar. 12, 2012.

Xu et al., "Monitoring Respiration With a Thermal Imaging System", U.S. Appl. No. 13/103,406, filed May 9, 2011.

Wang et al., "Multi-Band Infrared Camera System Optimized for Skin Detection", U.S. Appl. No. 13/416,436, filed Mar. 9, 2012.

Kyal et al., "Continuous Cardiac Pulse Rate Estimation From Multi-Channel Source Video Data", U.S. Appl. No. 13/528,307, filed Jun. 20, 2012.

Kyal et al., "Continuous Cardiac Signal Generation From a Video of a Subject Being Monitored for Cardiac Function", U.S. Appl. No. 13/871,766, filed Apr. 26, 2013.

* cited by examiner

CONTINUOUS CARDIAC PULSE RATE ESTIMATION FROM MULTI-CHANNEL SOURCE VIDEO DATA WITH MID-POINT STITCHING

CROSS REFERENCE TO RELATED APPLICATIONS

This patent application is a continuation-in-part of commonly owned U.S. patent application Ser. No. 13/528,307, "Continuous Cardiac Pulse Rate Estimation From Multi-Channel Source Video Data", by Kyal et al., filed Jun. 20, 2012, which is incorporated herein in its entirety by reference.

TECHNICAL FIELD

The present invention is directed to systems and methods for processing a time-series signal generated from video captured of a subject being monitored for cardiac function.

BACKGROUND

Our previous U.S. patent application Ser. No. 13/528,307, entitled: "Continuous Cardiac Pulse Rate Estimation From Multi-Channel Source Video Data", by Kyal et al., wherein a time-series signal 100 is processed to extract successive overlapping cardiac signals at 101A-H of FIG. 1. Previous segments of signals 101A-E are not shown because they run off the sheet. Each signal 101A-H has an endpoint or end-segment at 102A-H, respectively. To obtain continuous cardiac signal 103 for the subject of interest, these end-segments are stitched together. However, this method of endpoint stitching introduces artifacts, collectively at 104. The teachings hereof are specifically directed to resolving this particular issue.

BRIEF SUMMARY

What is disclosed is a novel system and method for extracting photoplethysmographic (PPG) signals (i.e., cardiac signals) on a continuous basis from signals generated from video images captured of a subject being monitored for cardiac function in a non-contact remote sensing environment. In one embodiment, a time-series signal is received. The time-series signal is generated from video images captured of a region of exposed skin where a PPG signal of a subject of interest can be registered. The time-series signal is then divided into batches for processing, with successive batches having at least a 95% overlap with a previous batch. Each of the batches of time-series signals is processed to obtain a PPG signal from each batch. A mid-point of each of these PPG-signals is stitched together to obtain a continuous PPG signal for the subject. The continuous PPG signal for the subject can then be viewed on a display device.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
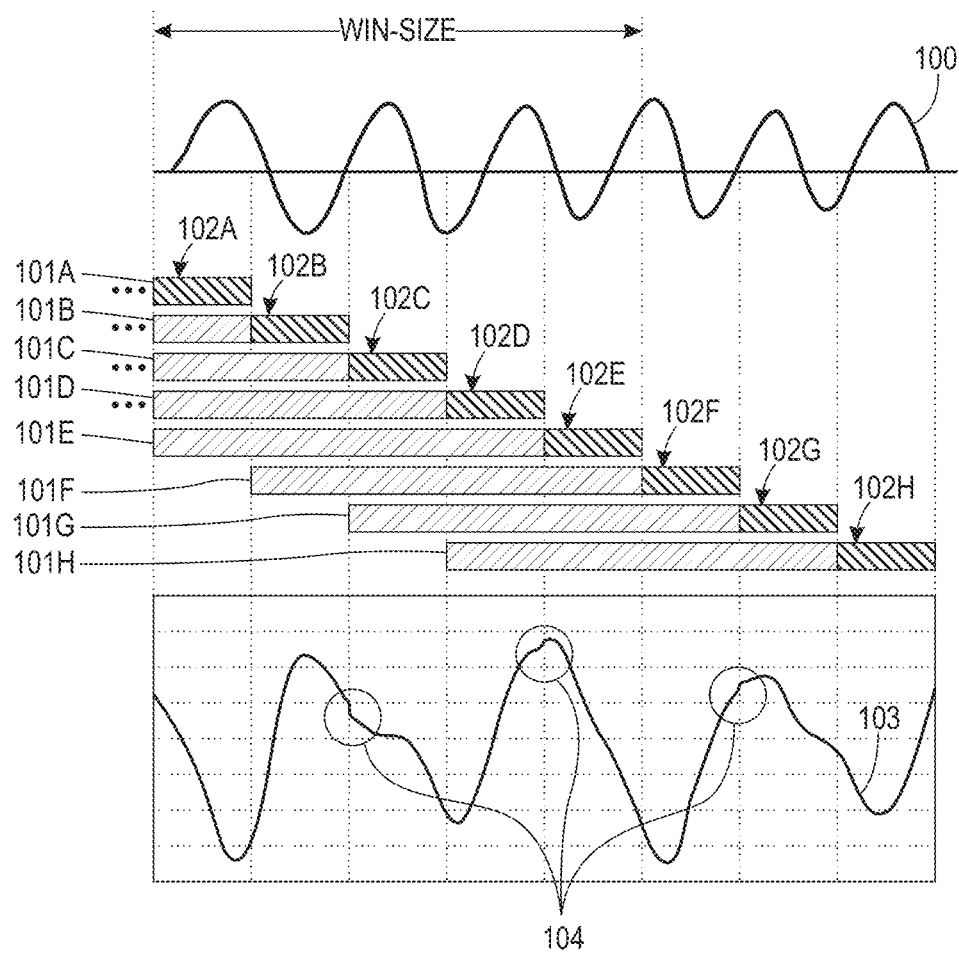
FIG. 1 illustrates an example prior art method which generates a continuous cardiac signal using endpoint stitching.

What is disclosed is a computationally efficient system and method for estimating a subject's cardiac pulse rate from multi-channel source video data that can be used in a continuous monitoring mode with a high degree of measurement accuracy.

NON-LIMITING DEFINITIONS

A "subject of interest", as used herein, refers to a human having a cardiac function. Although the term "human", "person", or "patient" may be used throughout this text, it should be appreciated that the subject of interest may be something other than a human being such as, for instance, an animal. Use of "person" or "patient" is not to be viewed as limiting the appended claims strictly to humans.

A "video" is a time-varying sequence of images captured using a video camera capable of acquiring video data over multiple data acquisition channels. The video may also contain other components such as, audio, time reference signals, and the like.

A "time-series signal" refers to a time varying signal generated from images of the captured video. The time-series signal generated from the captured video images can be RGB signals, IR signals, a combination of RGB and IR signals, multi-spectral signals, or hyperspectral signals. Time-series signals may be generated in real-time from a streaming video as in the case of continuous patient monitoring.

"Receiving a time-series signal" is intended to be widely construed and means to retrieve, receive, capture with a video capture device, or otherwise obtain a time-series signal for processing in accordance with the teachings hereof. In various embodiments, the time-series signal is retrieved from a remote device such as a computer workstation over a wired or wireless network or obtained on a continuous basis from a video stream.

A "sliding window" refers to a window of size win_size that identifies successive segments of a time-series signal for processing in accordance with the teachings hereof. The window has a size which can be different for one or more time-series signal segments. The window size can also be based on a performance characteristic of the blind source separation method used for constrained source separation. A cardiac signal is extracted from each batch of time-series signal. Each successive batch has at least a 95% overlap with a previous batch. The overlap must be significant enough to ensure consistency in signal recovery estimation.

A "seed reference signal" is a reference signal used to perform constrained source separation on a particular time-series signal segment. On each iteration of running constrained source separation, an estimated output signal is generated. If, as determined by a measure of closeness, the estimated output signal produced on the current iteration is not within a threshold level then the seed reference signal is updated to obtain an updated reference signal. In a manner as more fully described herein, the updated reference signal is used on a next iteration of constrained source separation performed on the current time-series signal segment to obtain another estimated source signal. On each iteration, a closeness measure is determined and, in response to the measure of closeness not being within a pre-defined threshold, the reference signal is again updated and constrained source separation is performed yet again. The process repeats until the estimated source signal is within a threshold limit or a pre-determined number of iterations have occurred. It should be appreciated that, on the first iteration, the seed reference signal is used for cICA processing of the current time-series signal segment, with the reference signal being updated for each successive iteration of cICA processing until a termination criteria is reached.

"Updating the reference signal" means changing at least one aspect of the reference signal. The reference signal may be updated by, for example, changing a frequency of the signal, or by changing an amplitude or phase of the signal. The reference signal may be updated by altering a waveform of the signal. The waveform can be, for example, a sine wave, a square wave, a user defined shape such as that obtained from an ECG signal, or a cardiac pulse waveform derived from apriori knowledge of the subject's cardiac history.

Figure 2:
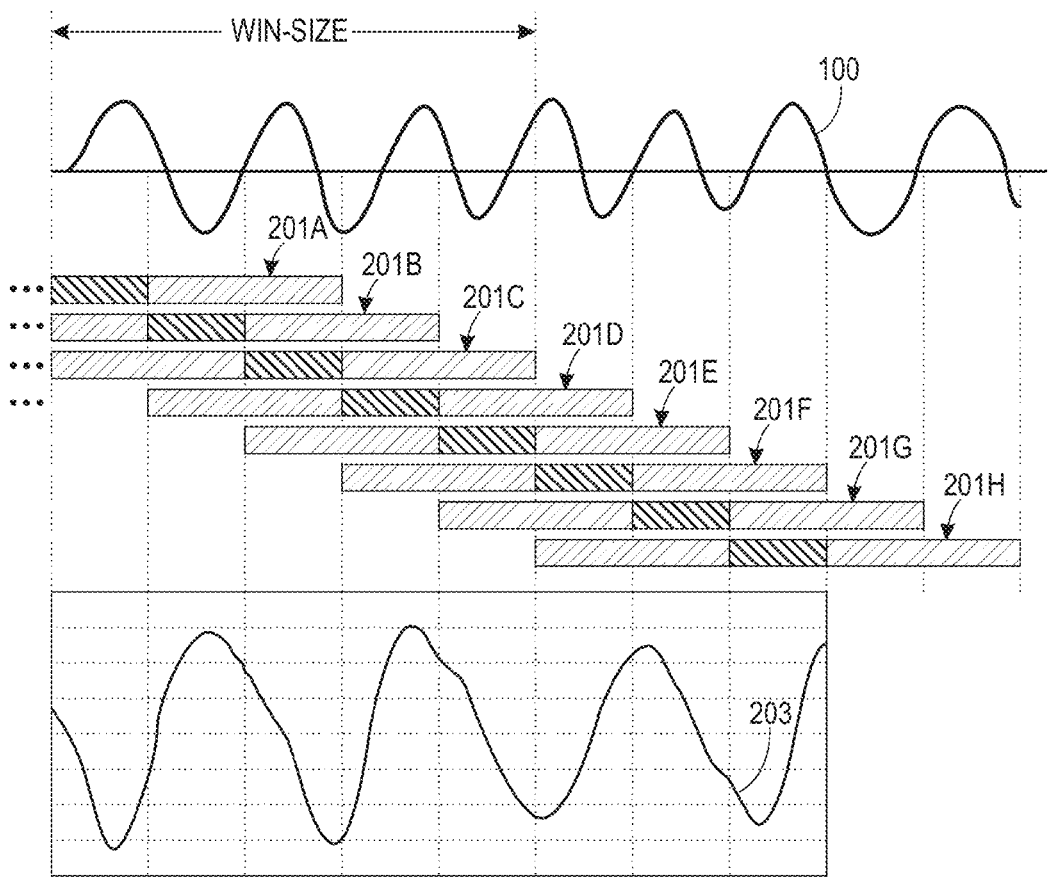
FIG. 2 illustrates the present method which generates a continuous cardiac signal using mid-point or mid-section stitching.

"Stitching via mid-points" means, according to the present method, connecting together mid-sections of extracted signals to obtain a continuous cardiac signal. Reference is now being made to FIG. 2 wherein the time-series signal 110 is processed by a sliding window of win_size which divides each of the extracted signals 201A-H into five segments. As previously discussed with respect to FIG. 1, continuous cardiac signal 103 was generated by stitching together the endpoints of each of the overlapping cardiac signals extracted from the time-series signal 103. The present method stitches together the mid-sections of each successive signal to obtain a continuous cardiac signal 203 that does not have artifacts.

"Conditioning the signal" means processing the estimated source signal to remove artifacts. Artifacts include undesirable periodic signals, background noise and other unwanted environmental factors. As disclosed herein, the conditioned signal becomes the seed reference signal used for to perform constrained source separation on the next time-series signal segment defined by the sliding window.

"Cardiac function" refers to the function of the heart and, to a large extent, to the cardio-vascular system. In most species, the heart comprises muscle which repeatedly contracts to pump blood throughout the vascular network. Cardiac function can be impacted by a variety of factors including age, stress, disease, overall health, and the like. Cardiac function can also be affected by environmental conditions such as altitude and pressure.

A "cardiac pulse" is a pressure wave that is generated by the subject's heart (in systole) as the heart pushes a volume of blood into the arterial pathway. Arterial movement, as a result of this pressure wave, can be sensed by tactile and electronic methods. A frequency of the cardiac pulse is the pulse rate measured over time, typically recorded in beats per minute (bpm). A resting adult human has a cardiac pulse rate of about 72 bpm. The frequency range of the human cardiac pulse is between about 50 bpm to 240 bpm. Each species have their own "normal" heart rate and thus their own cardiac pulse frequency range. Heart rate is proportional to the cardiac output, i.e., the volume of blood the heart can pump expressed in L/min (~5 L/min in an adult human). Cardio Output is often defined as: $CO=SV \cdot HR$, where SV is stroke volume and HR is heart rate (in bpm). Stroke volume can be affected by valvular dysfunction and ventricular geometric form.

"Blind Source Separation" is a technique for the recovery of unobserved signals from a mixed set of observed signals without any prior information being known about how the signals were mixed. Typically, the observed signals are acquired as output from sensors where each sensor receives or otherwise detects a different proportion of mixture of source signals. Blind source separation is a method for separating the source signals. One form of blind source separation is independent component analysis.

"Independent Component Analysis" (ICA) is a decomposition technique used for uncovering independent source signal components from a set of observations that are composed of linear mixtures of underlying sources, i.e., independent components of the observed data. These independent components (ICs), also called sources or factors, can be found by ICA methods. ICA is superficially related to principal component analysis. ICA is a powerful technique which is often capable of identifying underlying sources when classic methods have failed. Data analyzed by ICA can originate from many different kinds of applications including source signals comprising time-series signals. In practice, the ordering of the ICs is quite important to separate non-stationary signals or signals of interest with significant statistical characteristics. Constraints can be placed on this technique.

"Constrained source separation" is an independent component analysis method for separating time-series signals into additive sub-components using a reference signal as a constraint. Not all constraints can be used for constrained independent component analysis (cICA) because some constraints infringe classical ICA equivariant properties. Constraints that define or restrict the properties of the independent components should not infringe the independence criteria. Additional conditions can be incorporated using, for example, sparse decomposition of signals or fourth-order cumulants into the contrast function, to help locate the global optimum separating the components.

cICA is essentially a constraint minimization problem, i.e., minimize function C(y) subject to constraints: g(y:W)≤0 and/or h(y:W)=0, where C(y) is a contrast function, where constraints:

$$g(y:W)=[g_1(y:W),g_2(y:W),\ldots,g_v(y:W)]^T$$

and $$h(y:W)=[h_1(y:W),h_2(y:W),\ldots,h_v(y:W)]^T$$

define vectors of u (inequality) and v (equality), respectively. Statistical properties (e.g., consistency, asymptotic variance, robustness) of cICA depend on the choice of the contrast function C(y) and the constraints in the objective function.

More formally, let the time-varying observed signal be: $x=(x_1, x_2, \ldots, x_n)^T$, where x is a linear mixture of ICs $c_i$ of signal $c=(c_1, c_2, \ldots, c_m)^T$. Therefore, x=Ac where matrix A (of size n×m) represents the linearly mixed channels observing x. Demixing matrix W recovers components $c_1, c_2, \ldots, c_m$ of signal x which, in turn, produces signal y=Wx, given by: $y=(y_1, y_2, \ldots, y_m)^T$, with minimal knowledge of A and c. Reference signal $r=(r_1, r_2, \ldots, r_l)^T$ carries traces of information of desired signal c and need not be exact to the original sources. A measure of closeness is estimated between signal $y_i$ and reference signal $r_i$ by the norm $\epsilon(y_i,r_i)$. The components of output signal y are mutually independent and correspond to l original sources mixed in observed signal x. The matrix A is an m×m square matrix when there are m number of observed signals and m number of sources. Demixing matrix W is l×m (l<m). The minimum norm $\epsilon(y_i,r_i)$ of all outputs y indicates that signal $y_i$ is closest to reference signal $r_i$. If this component is closest to the reference signal then $E(y_i^*,r_i)<\epsilon(y_i^o,r_i)$, where $y_i=y_i^*$ is the output signal producing the desired IC closest to $r_i$, and $y_i^o$ is the next closest output signal. cICA recovers the closest IC if the closeness measure and threshold are properly selected. Success depends on the selection of threshold parameter $\xi_i$: $\epsilon(y_i^*,r_i)-\xi_i \leq 0$. None of the other m−1 sources will correspond to reference signal $r_i$ if $\xi_i$ is in the scalar range of $[\epsilon(y_i^*,r_i),\epsilon(y_i^o,r_i)]$. The reader is directed to the following texts: "*Independent Component Analysis*", ISBN-13: 978-0471405405, and "*Independent Component Analysis: Principles and Practice*", ISBN-13: 978-0521792981, which are incorporated herein in their entirety by reference.

Example Image Capturing System

Figure 3:
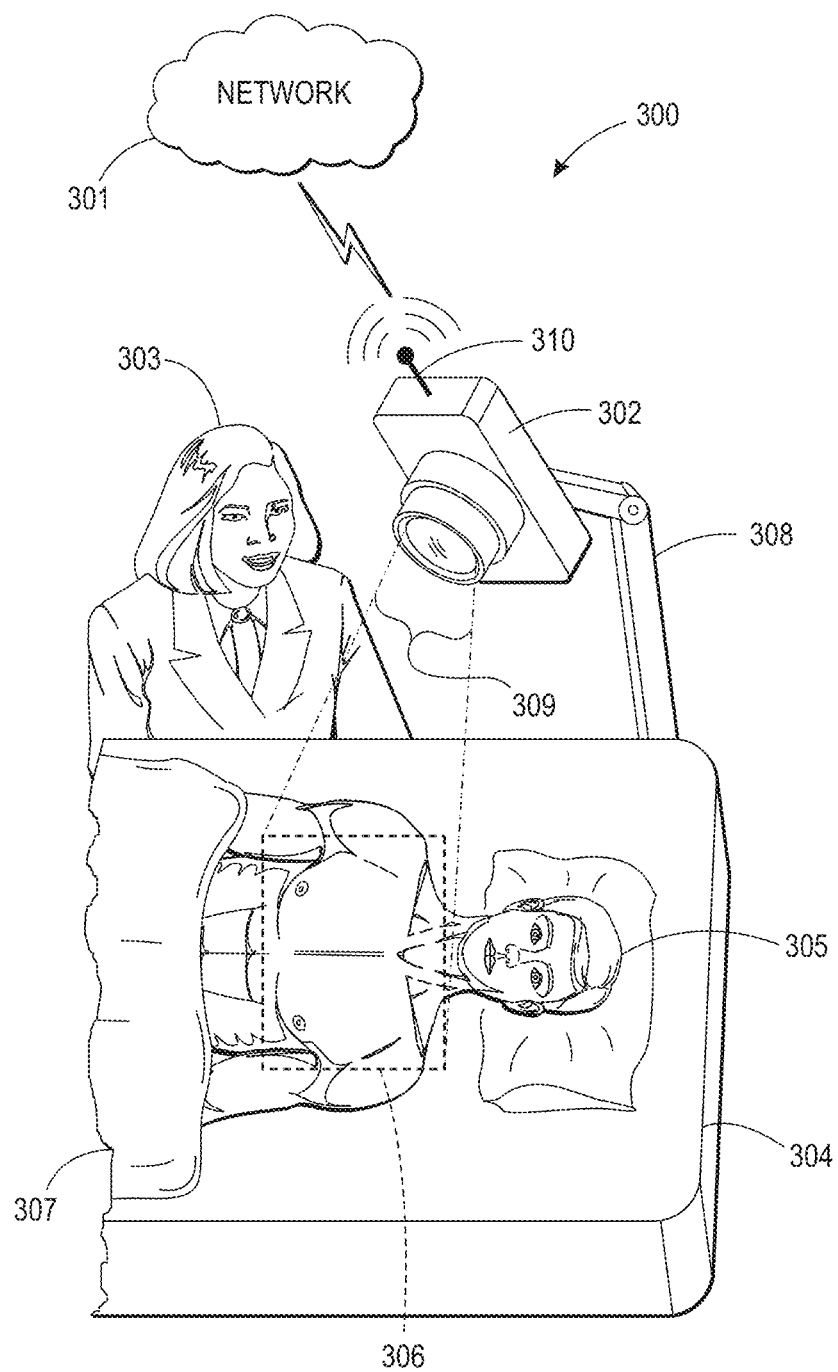
FIG. 3 illustrates an example system for capturing a multi-channel video signal of a subject of interest.

Reference is now being made to FIG. 3 which illustrates an example imaging system for capturing a multi-channel signal of a subject of interest.

Examination room 300 has an example image capturing system 302 being operated by technician 303 standing at the bedside 304 of subject of interest 305 shown resting his head on a pillow while most of his body is partially covered by sheet 307. Camera system 302 is rotatably fixed to support arm 308 such that the camera's field of view 309 can be directed by nurse 303 onto an area of exposed skin of a chest area 306 of patient 305 for continuous monitoring of cardiac function. Support arm 308 is on a set of wheels so that the image capture system can be moved from bed to bed and room to room. Although patient 305 is shown in a prone position lying in a bed, it should be appreciated that images of the subject of interest being monitored for cardiac function can be captured while the subject is positioned in other supporting devices such as, for example, a chair or wheelchair, standing up, including walking or moving. The embodiment of FIG. 3 is not intended to be viewed as limiting the scope of the appended claims in any respect. Camera system 302 captures video images of the subject of interest to be monitored for cardiac function. The captured video images comprises multi-channel source data such as RGB and/or multi-spectral acquired over time. Camera 302 comprises imaging sensors which may be a single sensor or a sensor array including a plurality of individual or separate sensor units. A central processor integral to camera 302 and in communication with a memory (not shown) and the imaging sensor may take a variety of forms each having the capability of detecting changes in the status of sensors and outputting an alarm, notice, report, and the like if a change in any hardware or software of the camera has been detected. Other sensors contemplated are capable of sensing a change of position or status of patient 305 and issue an alarm or notification via transmission element 310 to a nurse, doctor, or technician in the event that the cardiac function of the patient falls outside a set of pre-defined parameters. Antenna 310 is used to communicate the captured images to various remote devices. Transmitter 310 may be a wired (e.g., Ethernet) connection utilizing an Ethernet network consisting of Ethernet cables and an Ethernet hub that is in communication with a network 301. Camera system 302 may include both wireless and wired elements and may be connected via other means such as coaxial cable, radio frequency, Bluetooth, or any other manner for communicating data. Network 301 receives the transmitted video signals and wirelessly communicates the received signal data to devices such as, for instance, a workstation with a graphical display device, or a handheld device such as an iPhone, iPad, notebook, and the like. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Techniques for placing devices in networked communication are well established. Therefore, a further discussion as to specific techniques for networking devices has been omitted. Any of the networked devices may include a network interface card or system.

Example Block Diagram

Figure 4:
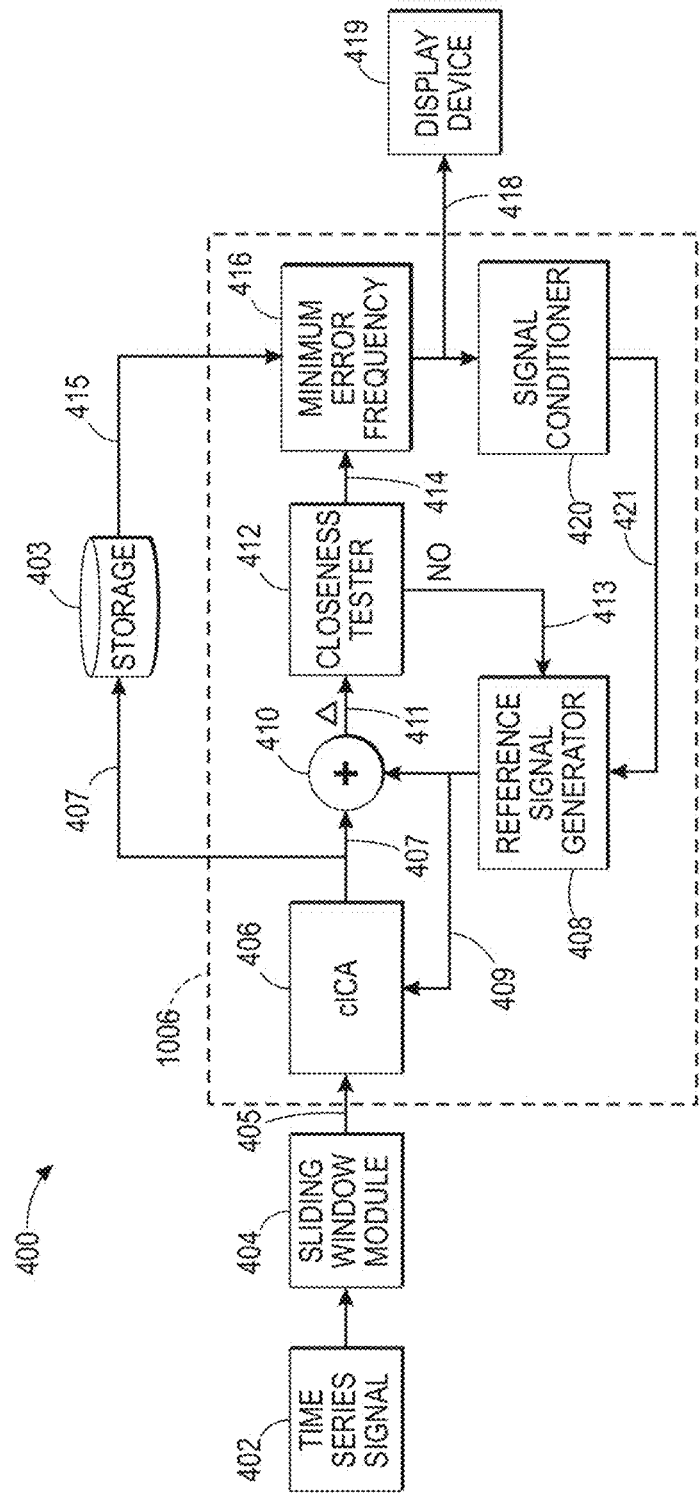
FIG. 4 is a block diagram of one embodiment of a signal processing system for performing various aspects of the present system and method.

Reference is now being made to FIG. 4 which is a block diagram of one embodiment of a signal processing system for performing various aspects of the present system and method for continuous cardiac pulse rate estimation.

Received time-series signal 402 is provided to sliding window module 404 which defines a sliding window of size win_size and, on each iteration, uses that sliding window to identify overlapping segments of the time-series signal for processing. The received time-series signal is generated from video images captured of a subject of interest being monitored for cardiac function in accordance herewith. On a first iteration, sliding window module 404 defines a first time-series segment 405 for processing. With each successive iterations, sliding window module 404 identifies a successive time-series signal segment 405 for processing. Between successive iterations, the overlap in data frames is significant enough to ensure consistency in signal recovery estimation. Reference signal generator 408 generates, on a first iteration, a seed reference signal 409 which has a frequency range that approximates a frequency range of the subject's cardiac pulse. On successive iterations, the reference signal generator conditions signal 416 to obtain a next reference signal for use in the next iteration. On each iteration, updated reference signal 409 is provided to cICA algorithm 406 which produces a next estimated source signal 407. Each of the produced estimated source signals 407 are provided to storage device 403. On each iterations, reference signal 409 is provided to comparator 410 wherein it is compared against the produced estimated source signal 407 such that a difference 411 therebetween can be determined. Closeness test module 412 determines whether the difference 411 between reference signal 409 and estimated source signal 407 are with a pre-defined threshold (or if a pre-determined number of iterations have occurred). If it is determined that closeness has not occurred then signal 413 is sent to reference signal generator 408 to update reference signal 409 by changing the reference signal frequency, amplitude, phase, and/or waveform. The updated reference signal is then again provided to cICA 406 which, on this iteration, produces a next estimated source signal 407. The next estimated source signal 407 produced by cICA 406 is again compared to reference signal 409 and a difference 411 therebetween determined. New difference 411 is provided to closeness tester 412 which again determines whether closeness has occurred to within a pre-defined threshold level (or if a pre-determined number of iterations have occurred). If closeness has not occurred then the process repeats. One of ordinary skill will recognize the iterative nature of the signal processing system of FIG. 4. Upon closeness (which terminates the current cycle of iterations), signal 414 is provided to minimum error frequency determinator 416 which retrieves the estimated source signals (collectively at 415) produced for the current time-series segment by cICA 406 and identifies which of the estimated source signals (307) had a minimum error, i.e., was closest to the reference signal. The frequency of the estimated source signal which achieved a minimum error is determined to be the estimated cardiac pulse rate 418 for the current time-series signal segment 405. In this embodiment, estimated cardiac pulse rate 418 is provided to display device 419. In other embodiments, the estimated cardiac pulse rate is provided to a processor to determine whether the pulse rate is within acceptable parameters set for the subject, and an alert signal is transmitted to a monitoring device in the event that the estimated cardiac pulse rate, for any given segment, is outside an acceptable limit or range. For the next time series segment 405, the closest estimated output signal 418, as determined by the previous iteration, is provided to signal conditioner 420 wherein signal 418 is conditioned by removing artifacts. One method for conditioning a time-series signal may involve constructing a square wave or a sine wave or a user defined shape such as that obtained from an ECG signal or a PPG signal and is disclosed in U.S. patent application entitled: "Estimating Cardiac Pulse Recovery From Multi-Channel Source Data Via Constrained Source Separation", U.S. patent application Ser. No. 13/247,683, by Mestha et al, which is incorporated herein in its entirety by reference. The conditioned signal is provided to reference signal generator 408 and is used as seed reference signal to initiate processing of the next time-series segment until closeness is determined (or a pre-determined number of iterations have occurred). The frequency of the closest estimated source signal is determined to be the subject's estimated cardiac pulse rate, for this particular time-series signal segment. The process repeats for each time-series signal segment defined by the sliding window until all signal segments have been processed or until a termination criteria is met.

Although the block diagram of FIG. 4 shows an embodiment wherein current result 418 is conditioned and used as a seed reference signal for the next successive time-series segment, it should also be appreciated that any of the resulting signals 418 obtained as a result of having processed any of the previous segments 405 can be used as a seed reference signal to initiate processing of the current time-series signal segment.

Flow Diagram of One Embodiment

Figure 5:
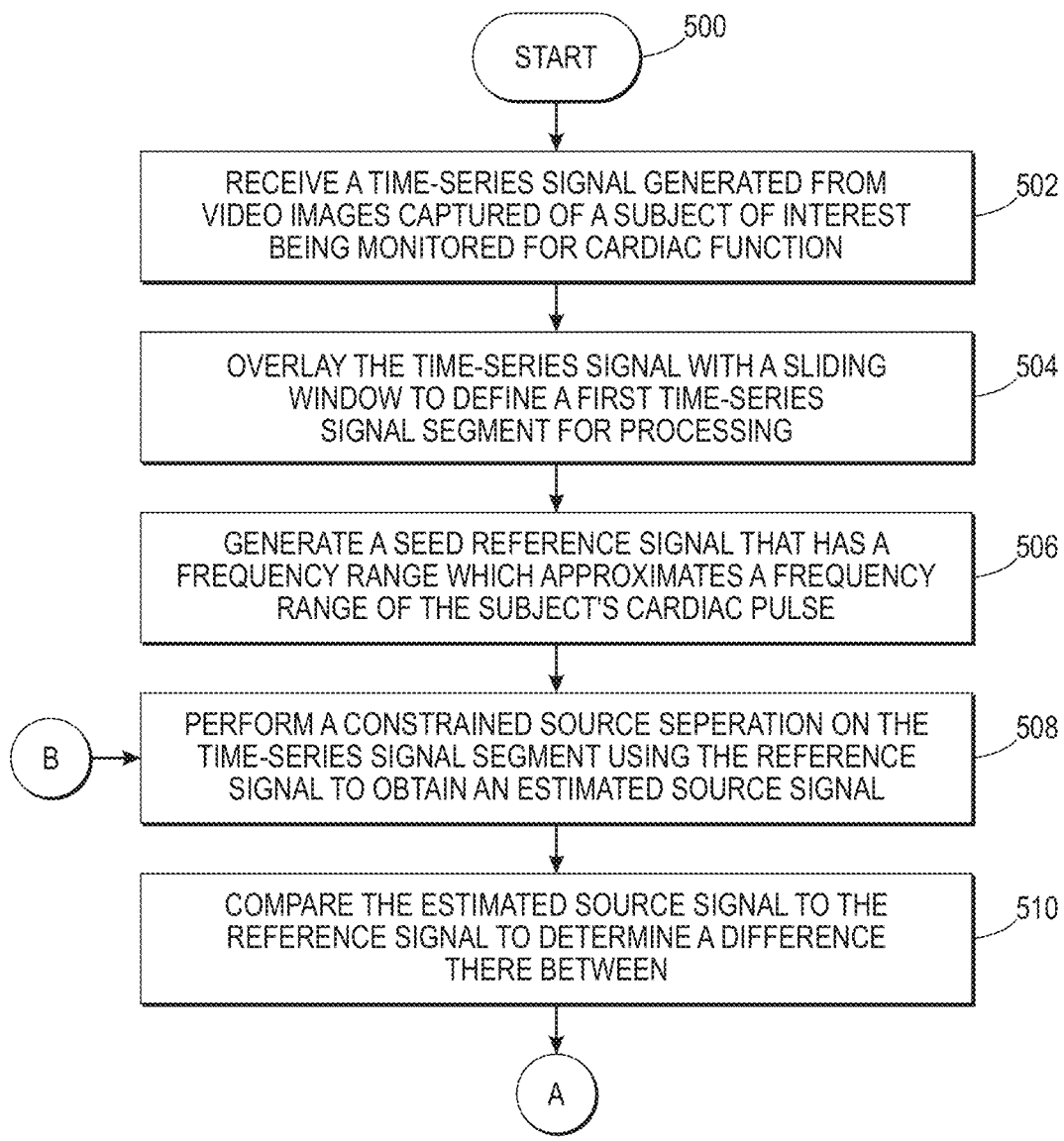
FIG. 5 is a flow diagram which illustrates one embodiment of the present method for continuous cardiac pulse rate estimation.

Reference is now being made to the flow diagram of FIG. 5 which illustrates one embodiment of the present method for continuous cardiac pulse rate estimation. Flow processing starts at step 500 and immediately proceeds to step 502.

At step 502, receive a time-series signal generated from video images captured of a subject of interest intended to be monitored for cardiac function. The received time-series signal can be RGB signals, IR signals, RGB and IR signals, multi-spectral signals, or hyperspectral signals.

At step 504, overlay the time-series signal with a sliding window of size win_size to define a first time-series signal segment for processing.

At step 506, generate a seed reference signal which has a frequency range which approximates a frequency range of the subject's cardiac pulse. The reference signal can be received from a remote device over a network or retrieved from a memory, storage device, or obtained from a database of reference signals.

At step 508, perform constrained source separation on the time-series signal segment using a reference signal. Each iteration of the constrained source separation method produces an estimated source signal.

At step 510, compare the estimated source signal to the reference signal (used in step 508) to determine an amount of a difference therebetween. This difference is the error between the estimated source signal produced as a result of having performed step 508, and the reference signal.

Figure 6:
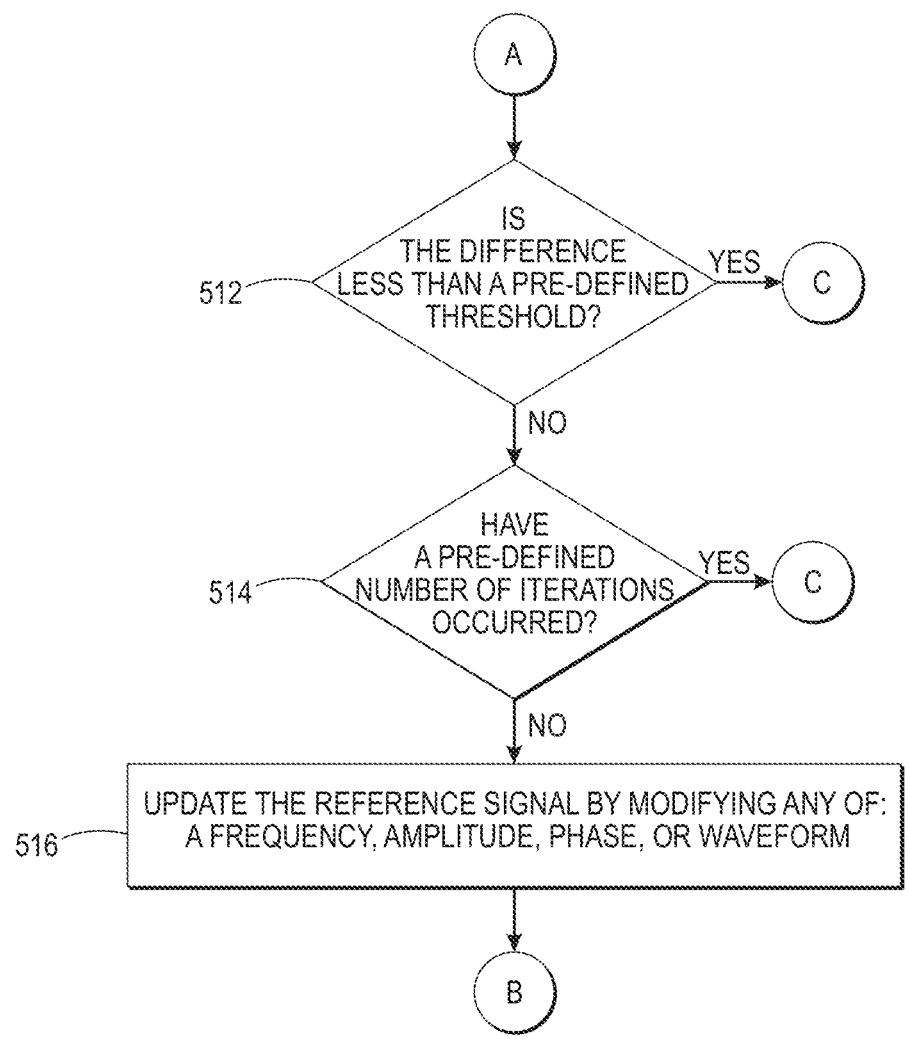
FIG. 6 is a continuation of the flow diagram of FIG. 5 with flow processing continuing with respect to node A.

Reference is now being made to the flow diagram of FIG. 6 which is a continuation of the flow diagram of FIG. 5 with flow processing continuing with respect to node A.

At step 512, a determination is made whether the difference (of step 510) is within a pre-determined threshold value. If not then processing continues with respect to step 514 wherein a determination is made whether a pre-defined number of iterations have occurred. If not then processing continues with respect to step 516 wherein the reference signal is updated. As discussed, the reference signal may be updated by changing any a frequency, an amplitude, a phase, shape and a waveform of the reference signal. Changing the waveform may comprise changing any of: a sine wave, a square wave, a user-defined shape obtained from an ECG signal, and/or a cardiac pulse waveform derived from the subject. Upon having updated the reference signal in step 516, processing repeats with respect to node B wherein, at step 508. constrained source separation is again performed on the current time-series signal segment using the updated reference signal. Constrained source separation produces a next estimated source signal which, at step 510, is compared to the updated reference signal to determine an amount of an error therebetween. If, at step 512, the difference is not less than a pre-defined threshold and, at step 512, a pre-determined number of iterations have not yet occurred then, at step 516, the reference signal is again updated. Processing repeats in such a manner until the occurrence of either the difference (of step 512) is less than the pre-defined threshold or a pre-determined number of iterations have occurred (of step 514). If, at step 512, the difference produced as a result of the comparison of step 510 is less than the pre-defined threshold then processing continues with respect to node C. If, at step 514, the pre-defined number of iterations has occurred then processing continues also with respect to node C.

Figure 7:
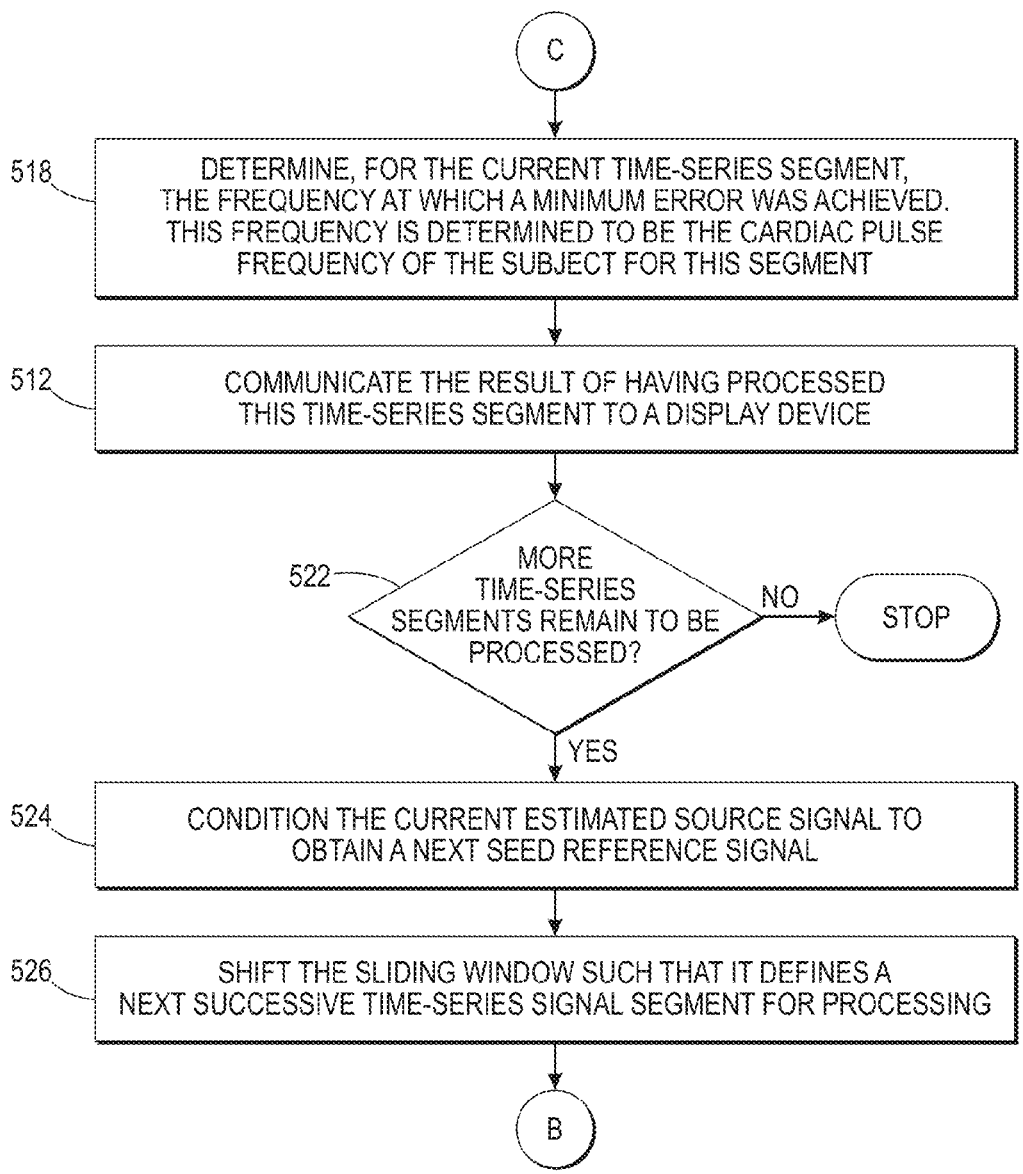
FIG. 7 is a continuation of the flow diagram of FIG. 6 with flow processing continuing with respect to node C.

Reference is now being made to the flow diagram of FIG. 7 which is a continuation of the flow diagram of FIG. 6 with flow processing continuing with respect to node C.

At step 518, the frequency at which a minimum error was achieved (between the estimated source signal and the reference signal of step 510) is determined for the current time-series signal segment being processed. This frequency is determined to be the subject's estimated cardiac pulse rate for the current time-series segment (of step 504).

At step 520, the result (of step 518) is communicated to a display device. The results may be further processed for a determination as to whether the subject's estimated cardiac pulse rate is within acceptable limits. If not then a signal can be generated to notify, for example, the patient's cardiac physician or a nurse.

At step 522, a determination is made whether more time-series signal segments remain to be processed. If not then, in this embodiment, further processing stops. Otherwise, processing continues with respect to step 524.

At step 524, condition the estimated source signal with the minimum error (of step 518) to produce a next reference signal to be used by the constrained source separation algorithm to processed the next time-series signal segment.

At step 526, shift the sliding window such that it defines a next successive time-series signal for processing. Each successive shifting of the sliding window at least partially overlapping the previous time-series signal segment. The overlap in data frames is preferably significant enough to ensure consistency in signal recovery estimation. This will depend, to a large extent, on the time-series signals being processed and may be determined by trial and error or based upon past experience in processing such signals. Once a next time-series signal segment has been identified, processing repeats with respect to node B wherein constrained source separation is performed on this signal segment using the next reference signal (of step 524). Processing continues in such a manner until, at step 522, it is determined that no more time-series signal segments remain to be processed, and further processing stops.

It should be appreciated that the flow diagrams hereof are illustrative. One or more of the operative steps illustrated in any of the flow diagrams may be performed in a differing order. Other operations, for example, may be added, modified, enhanced, condensed, integrated, or consolidated with the steps thereof. Such variations are intended to fall within the scope of the appended claims. All or portions of the flow diagrams may be implemented partially or fully in hardware in conjunction with machine executable instructions.

Example Sliding Window Defining Overlapping Signal Segments

Figure 8:
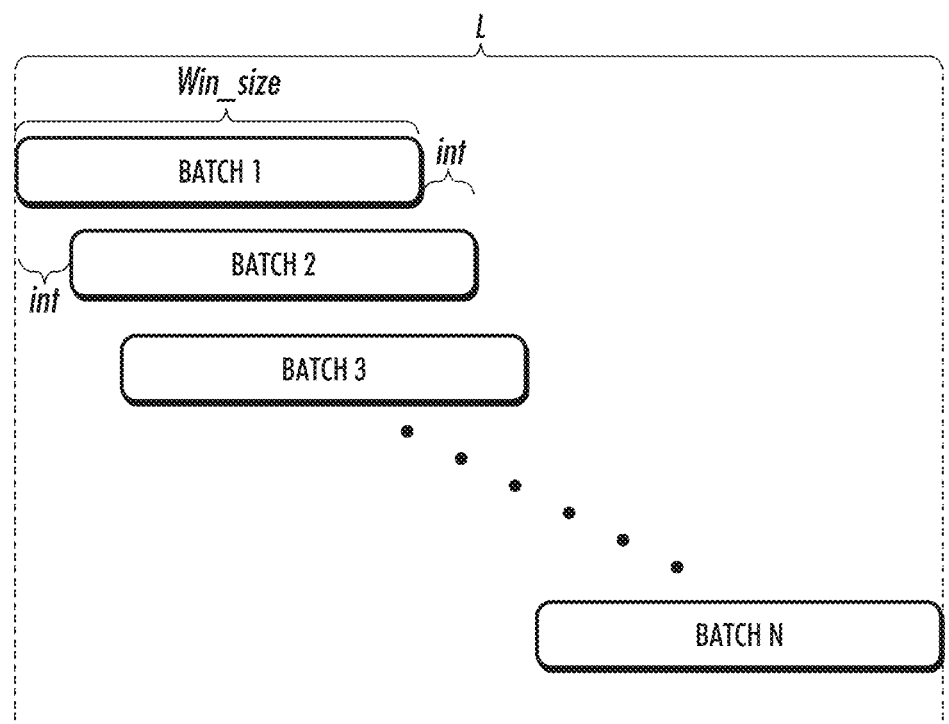
FIG. 8 illustrates a sliding window which is repeatedly shifted to define overlapping successive time-series signal segments for processing in accordance with various embodiments hereof.

Reference is now being made to FIG. 8 which illustrates a sliding window which is repeatedly shifted to define overlapping successive time-series signal segments for processing in accordance with various embodiments hereof.

Video frames are spatially averaged over all pixels per frame to obtain RGB time varying signals or raw traces. Batches are created by sliding a window of length 30 seconds with 95% overlap between consecutive batches which means using only 1 second of new frames and retaining 29 seconds of frames from previous batch. However, the window length and the overlap length are resizable depending on rate of change of patient's pulse rate.

Functional Block Diagram for Continuous Cardiac Pulse Rate Monitoring

Figure 9:
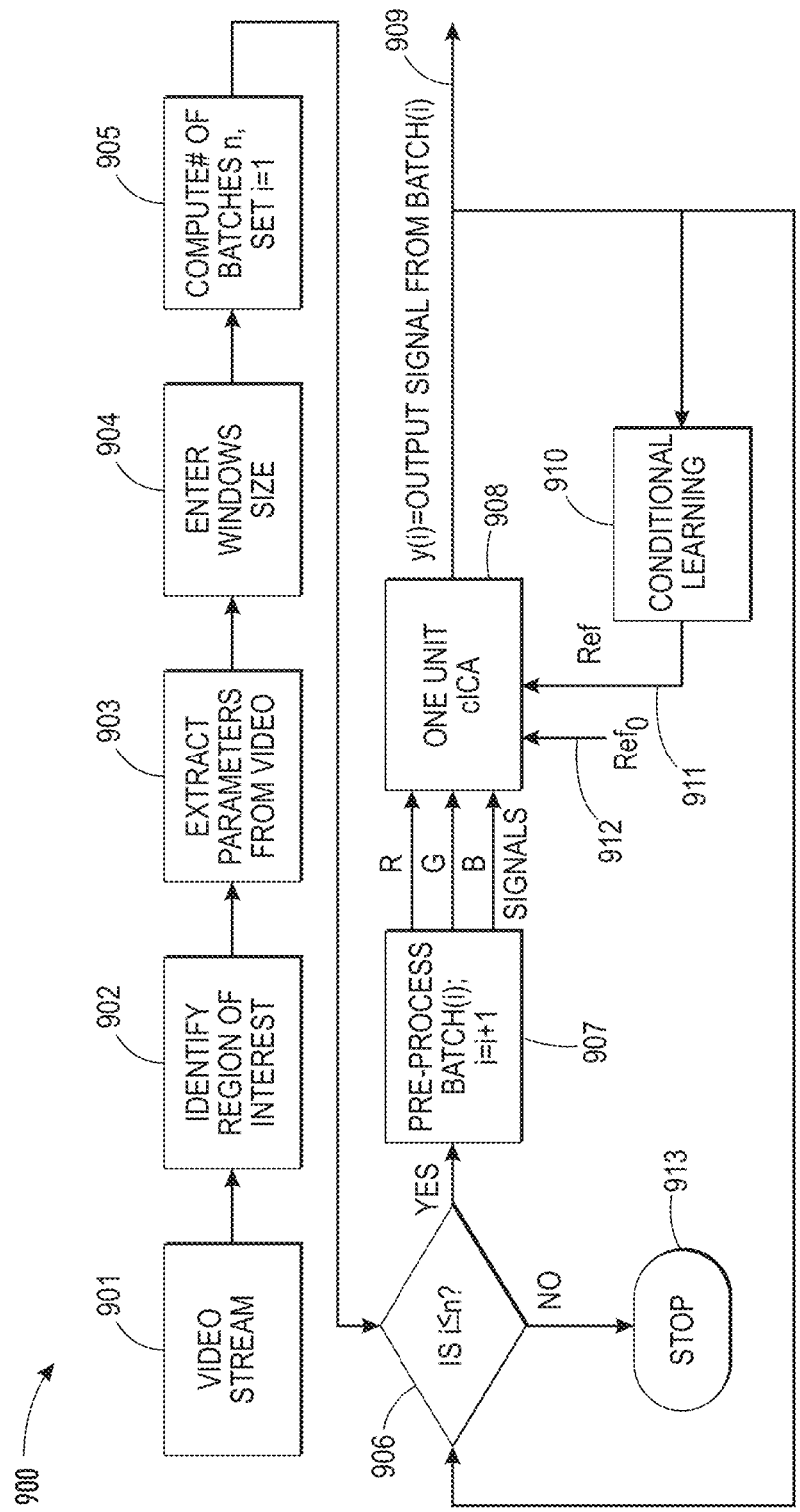
FIG. 9 shows an example block diagram of one embodiment of the present method for continuous pulse rate monitoring with computational blocks for a video stream comprised of n number of batches, the functional steps being repeated as new video streams arrive.

Reference is now being made to FIG. 9 which illustrates an example functional block diagram 900 of an embodiment for continuous pulse rate monitoring with computational blocks for a video stream comprised of n number of batches, the functional steps being repeated as new video streams arrive. In block 901, the video stream is captured and provided to video pre-processing block 902 wherein regions of interest of the subject being monitored are identified or otherwise selected. In block 903, parameters are extracted from the video such as video length, frame speed, and the like. In block 904, the user enters various parameters such as window size, threshold level, max number of iterations, and the like. In block 905, the number of batches n is computed based upon the length of the time-series signal and the size of the user-defined window. Batch counter i is initialized to 1. On the first iteration, a determination is made (in decision block 906) whether batches remain to be processed. If so then, in block 907, the current batch is pre-processed which includes continuous time band pass filtering (with an adjustable bandwidth depending on patient's pulse rate), whitening and normalizing. The pre-processed R, G, B signals associated with the time-series signal segment defined by the current window. The batch counter is incremented. In block 908, constrained source separation is performed on the time-series signal segment using, on a first iteration, the seed reference signal 912. A result of having performed constrained source separation is output signal y(i) corresponding to batch(i). Constrained source separation is performed on processed signals with the PPG signal measured from a Biopac system (or a square wave generated by incorporating prior knowledge about the patient's pulse rate) is used as reference $Ref_0$ to batch #1. cICA is based on constrained optimization using Newton-like learning to separate underlying source which is not identical but close to the reference signal (to within a measure of closeness). The output signal 909 resembles a PPG signal and pulse rate, and is computed by taking the Fast Fourier Transform (FFT) of this signal. On successive iterations, each output signal 909 corresponding to the previous batch is used by Conditional Learning Block 910 to learn the next reference signal 911 for the next batch such that pulse signals can be extracted for the next successive batch. If the pulse rate generated from the current batch exceeds the pulse rate generated from the previous batch (as measured by a pre-defined threshold value such as, for example, 13 bpm) the current estimated pulse rate is rejected and the previous pulse rate is retained in order to avoid an undesired jump in pulse rate caused by certain artifacts. This loop continues until all batches are processed and a continuous pulse rate achieved for the subject over time.

Example Functional Block Diagram

Figure 10:
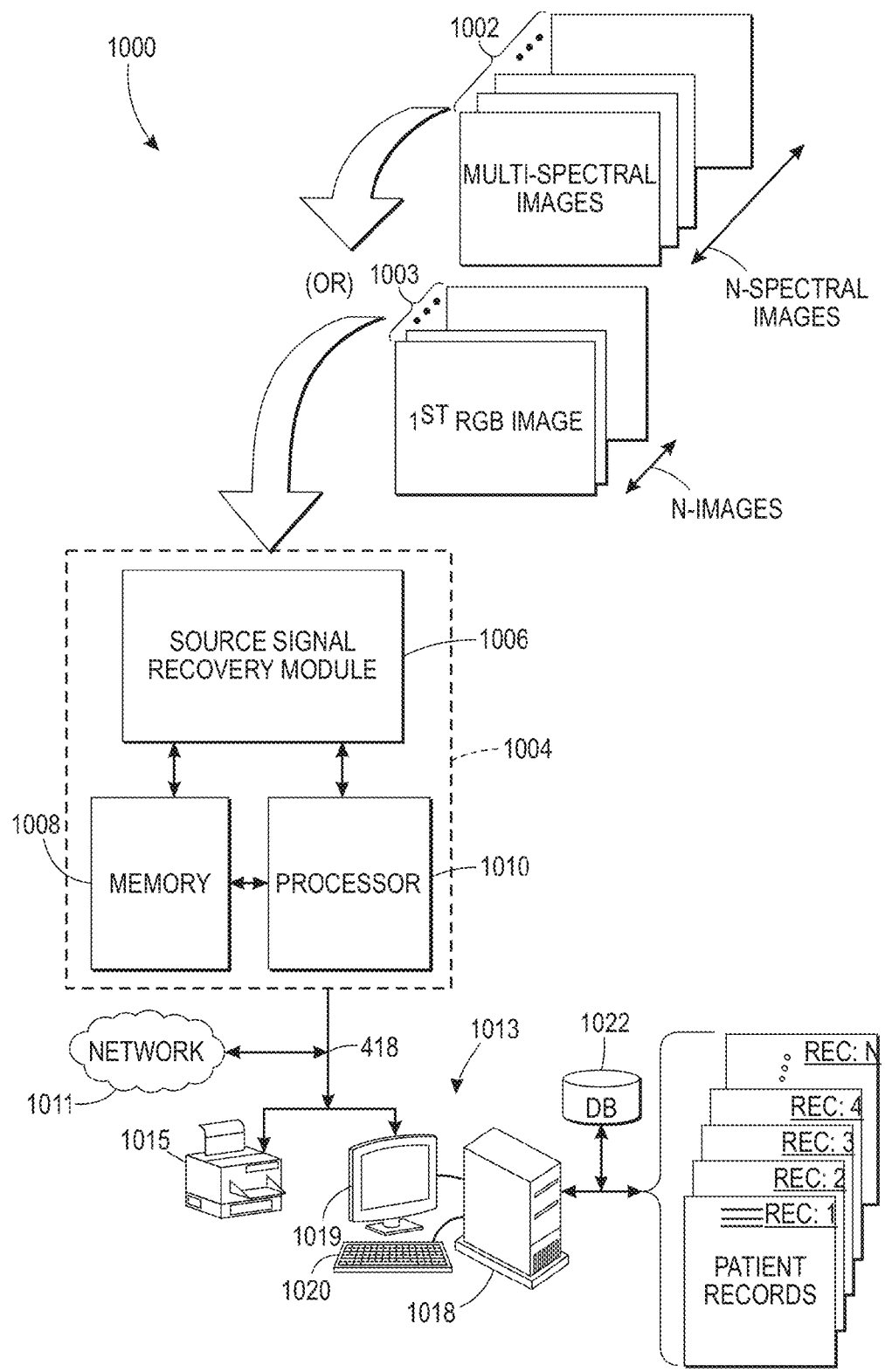
FIG. 10 illustrates a block diagram of one example signal processing system for performing various aspects of the present method as shown and described with respect to the flow diagrams of FIGS. 5-7.

Reference is now being made to FIG. 10 which illustrates a block diagram of one example processing system 1000 for implementing various aspects of the present method described with respect to the flow diagrams of FIGS. 5-7.

The system of FIG. 10 receives a sequence of video images captured of a subject of interest intended to be monitored for cardiac function. The captured video images are either a plurality of multi-spectral images 1002 captured using a multi-spectral camera or a plurality of RBG images 1003. The sequence of images 1002 or 1003 collectively comprises multi-channel source data acquired over time. Signal processing system 1004 receives the multi-channel source data into source signal recovery module 1006 which performs all the functionality as described in embodiment of FIG. 4. Memory 1008 and CPU 1010 facilitate the processing and output an estimated cardiac pulse rate 418. Estimated cardiac pulse rate 418 is communicated to workstation 1013 and multi-function print system device 1015 for further processing or for rendering. The estimated cardiac pulse rate may further be communicated to remote devices over network 1011. Many aspects of network 1011 are commonly known and a further discussion as to the construction and/or operation of a specific network configuration has been omitted. Suffice it to say, data is transmitted in packets between networked devices via a plurality of communication devices and links using established protocols. Data is transferred in the form of signals which may be, for example, electronic, electromagnetic, optical, light, or other signals. These signals are provided to a communications device such as a server which transmits and receives data packets by means of a wire, cable, fiber optic, phone line, cellular link, RF, satellite, or other medium or communications pathway. Computer workstation 1013 is shown comprising a computer case 1018 housing a motherboard, CPU, memory, interface, storage device, and a communications link such as a network card. The computer workstation is also shown having a display device 1019 such as a CRT, LCD, or touchscreen display. An alphanumeric keyboard 1020 and a mouse (not shown) effectuate a user input. In the embodiment of FIG. 10, computer system 1013 implements database 1022 wherein various records are stored, manipulated, and retrieved in response to a query. Although the database is shown as an external device, the database may be internal to computer case 1018 mounted on a hard disk housed therein. A record refers to any data structure capable of containing information which can be indexed, stored, searched, and retrieved in response to a query. Patient information can be stored and/or retrieved to any of the records in database 1022. It should be appreciated that the workstation has an operating system and other specialized software configured to display a variety of numeric values, text, scroll bars, pull-down menus with user selectable options, and the like, for entering, selecting, or modifying information displayed on the display device.

Any of the modules and processing units of FIG. 10 are in communication with workstation 1013 via pathways (not shown) and may further be in communication with one or more remote devices over network 1011. It should be appreciated that some or all of the functionality for any of the modules of system 1004 may be performed, in whole or in part, by components internal to workstation 1013 or by a special purpose computer system. It should also be appreciated that various modules may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through network 1011.

Performance Results

Figure 11:
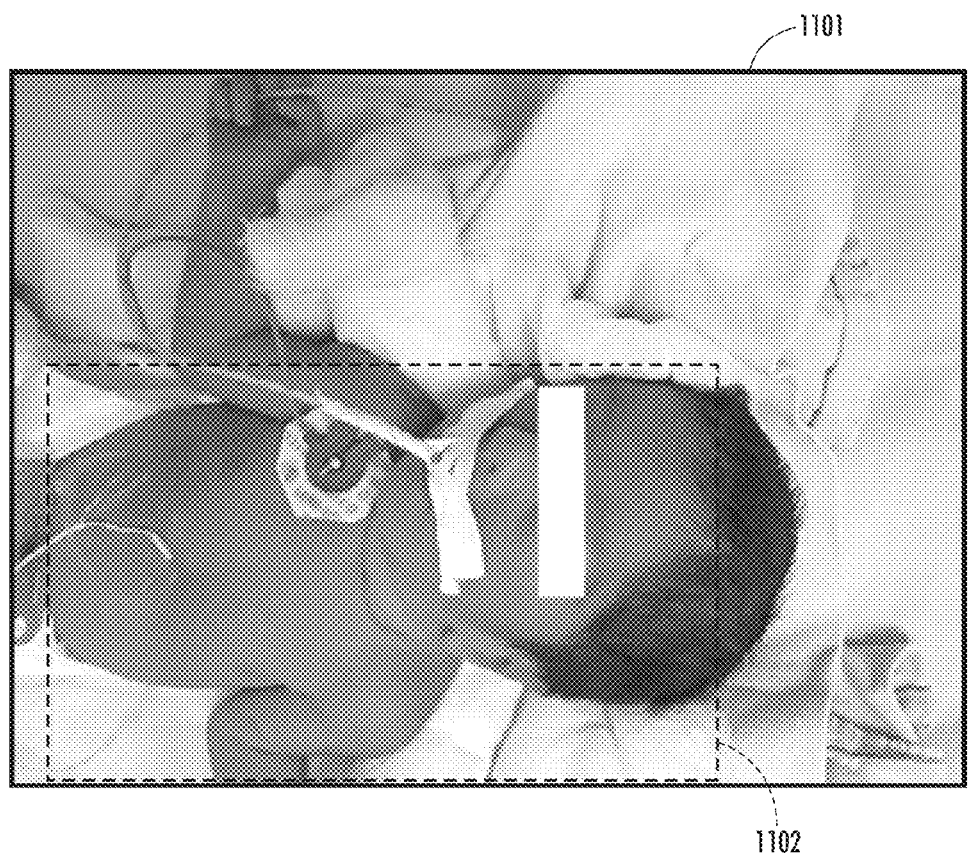
FIG. 11 shows an image of an infant in a neonatal intensive care unit (NICU) with a region of interest of exposed skin being identified using custom software.
Figure 12:
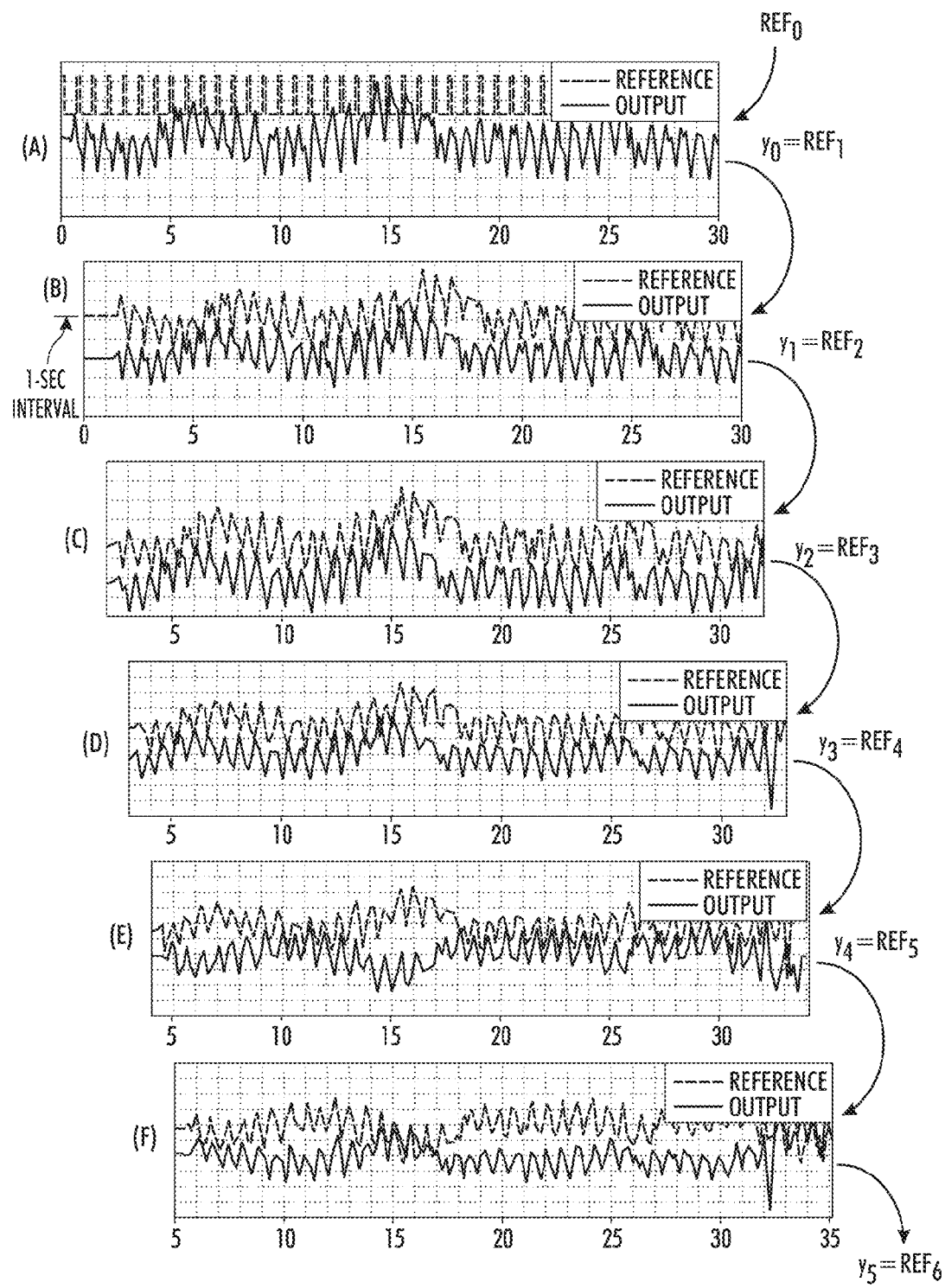
FIG. 12 shows pulse signals extracted from a video of the infant of FIG. 11 via successive overlapping batch processing in accordance with the present method.

In order to illustrate the effect of continuous pulse monitoring, video recordings were produced using a standard RGB digital camera at 30 frames per second (fps) with pixel resolution of 1280×720 and saved in AVI format. Each video was of length two minutes and was captured on infants in a neonatal ICU environment. A custom algorithm was used to detect a region of interest (ROI) comprising human skin in video frames, FIG. 11 shows an image 1101 of an infant in a neonatal intensive care unit (NICU) with a region of interest 1102 of exposed skin being identified in the video stream using custom software. The frames of the video were reduced to raw traces (RGB channels) with respect to time by spatially averaging all pixels in the ROI in each frame. The RGB traces were pre-processed, which included bandpass filtering to the expected pulse rate range of the infant, whitening followed by normalizing to yield traces of zero-mean unit-variance signal. The processed traces were fed to the one-unit cICA (908 of FIG. 9) with the conditioned PPG signal obtained from a Biopac system from the same infant. The frames were batch processed using a 30 second sliding window with 1 second increments. For each batch, the output from a previous batch was incorporated as prior knowledge to the cICA. FIG. 12 shows pulse signals extracted from a video of the infant of FIG. 11 via successive overlapped batch processing in accordance with the present method. Pulse computation for the first batch is shown in FIG. 12 at plot (A) where the seed reference signal $Ref_0$ is used to perform constrained source separation on the first time-series signal segment defined by the window of size win_size=30 to obtain estimated output signal ($y_0$) on the first iteration. The obtained estimated output signal $y_0$ serves as reference $Ref_1$ for the one-unit cICA to obtain next estimated source signal $y_1$ and so on in a sequential manner for successive batches (B) through (F), until all the time-series signal segments have been processed accordingly.

Example Special Purpose Computer

Figure 13:
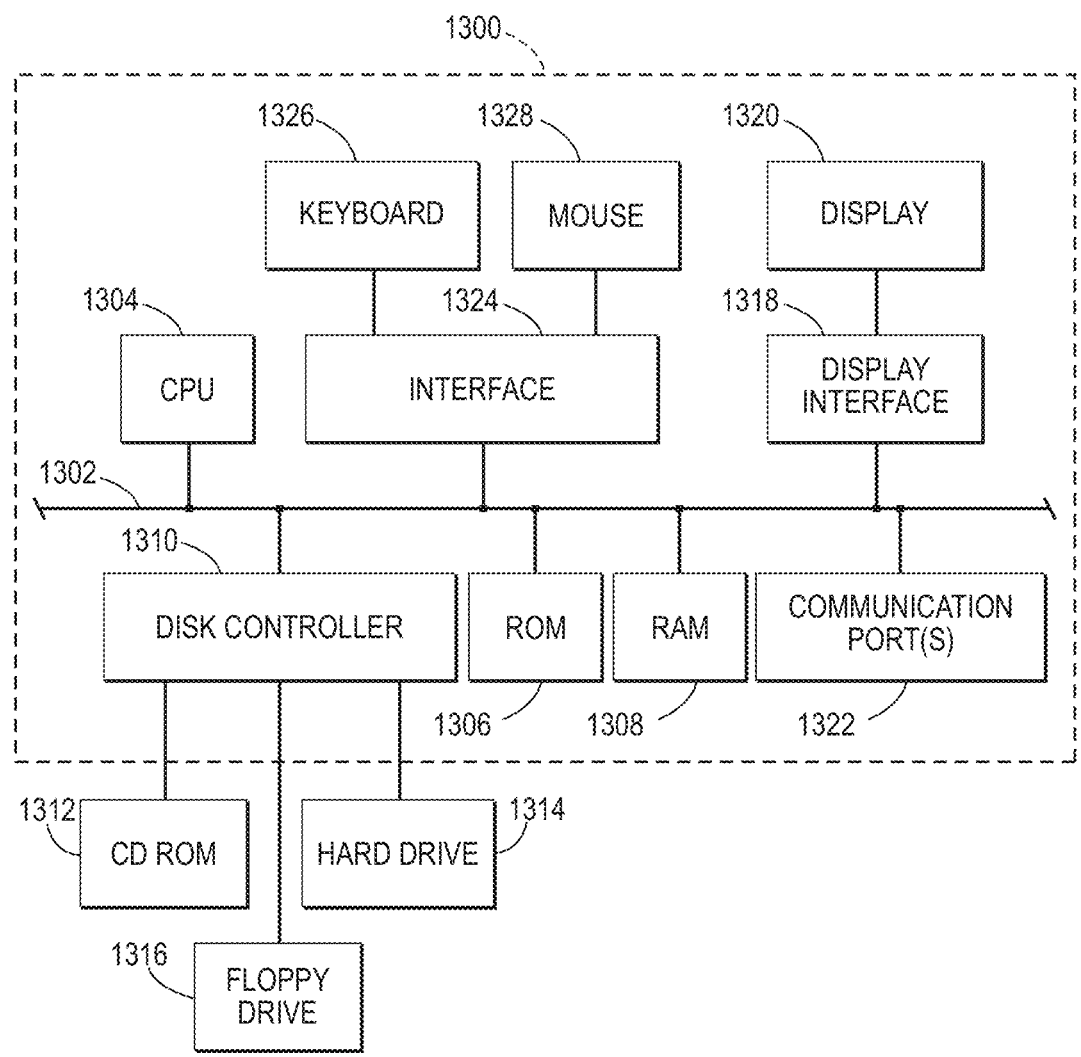
FIG. 13 illustrates a block diagram of one example special purpose computer for implementing one or more aspects of the present method as described with respect to the flow diagrams of FIGS. 5-7, and the block diagrams of FIGS. 4 and 9.

Reference is now being made to FIG. 13 which illustrates a block diagram of one example special purpose computer 1300 for implementing one or more aspects of the present method as described with respect to the flow diagrams of FIGS. 5-7, and the block diagrams of FIGS. 4 and 9. Such a special purpose processor is capable of executing machine executable program instructions and may comprise any of a micro-processor, micro-controller, ASIC, electronic circuit, or any combination thereof.

In FIG. 13, communications bus 1302 is in communication with a central processing unit (CPU) 1304 capable of executing machine readable program instructions for performing any of the calculations, comparisons, logical operations, and other program instructions for performing any of the steps described above with respect to the flow diagrams and the block diagrams hereof. Processor 1304 is in communication with memory (ROM) 1306 and memory (RAM) 1308 which, collectively, constitute example storage devices. Such memory may be used to store machine readable program instructions and other program data and results to sufficient to carry out any of the functionality described herein. Disk controller 1310 interfaces with one or more storage devices 1314 which may comprise external memory, zip drives, flash memory, USB drives, or other devices such as CD-ROM drive 1312 and floppy drive 1316. Storage device stores machine executable program instructions for executing the methods hereof. Such storage devices may be used to implement a database wherein various records are stored. Display interface 1318 effectuates the display of information on display 1320 in various formats such as, for instance, audio, graphic, text, and the like. Interface 1324 effectuates a communication via keyboard 1326 and mouse 1328, collectively a graphical user interface. Such a graphical user interface is useful for a user to enter information about any of the displayed information in accordance with various embodiments hereof. Communication with external devices may occur using example communication port(s) 1322. Such ports may be placed in communication with any of the example networks shown and described herein, such as the Internet or an intranet, either by direct (wired) link or wireless link. Example communication ports include modems, network cards such as an Ethernet card, routers, a PCMCIA slot and card, USB ports, and the like, capable of transferring data from one device to another. Software and data is transferred via the communication ports in the form of signals which may be any of digital, analog, electromagnetic, optical, infrared, or other signals capable of being transmitted and/or received by the communications interface. Such signals may be implemented using, for example, a wire, cable, fiber optic, phone line, cellular link, RF, or other signal transmission means presently known in the arts or which have been subsequently developed.

It will be appreciated that the above-disclosed and other features and functions, or alternatives thereof, may be desirably combined into many other different systems or applications. Various presently unforeseen or unanticipated alternatives, modifications, variations, or improvements therein may become apparent and/or subsequently made by those skilled in the art which are also intended to be encompassed by the following claims. Various changes to the above-described embodiments may be made without departing from the spirit and scope of the invention. The teachings hereof can be implemented in hardware or software using any known or later developed systems, structures, devices, and/or software by those skilled in the applicable art without undue experimentation from the functional description provided herein with a general knowledge of the relevant arts. Furthermore, the teachings hereof may be partially or fully implemented in software using object or object-oriented software development environments that provide portable source code that can be used on a variety of computer, workstation, server, network, or other hardware platforms. One or more of the capabilities hereof can be emulated in a virtual environment as provided by an operating system, specialized programs or leverage off-the-shelf computer graphics software such as that in Windows, Java, or from a server or hardware accelerator or other image processing devices.

One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology described herein. The article of manufacture may be included as part of an operating system, a plug-in, or may be shipped, sold, leased, or otherwise provided separately either alone or as part of an add-on, update, upgrade, or product suite. It will be appreciated that various of the above-disclosed and other features and functions, or alternatives thereof, may be combined into other systems or applications. Various presently unforeseen or unanticipated alternatives, modifications, variations, or improvements therein may become apparent and/or subsequently made by those skilled in the art which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for extracting photoplethysmographic (PPG) signals (i.e., cardiac signals) on a continuous basis from signals generated from batches of video images captured of a subject being monitored for cardiac function in a non-contact remote sensing environment, the method comprising:
    receiving a time-series signal generated from video images captured of a region of exposed skin where a photoplethysmographic (PPG) signal of a subject of interest can be registered;
    dividing said time-series signal into batches for processing, with successive batches having at least a 95% overlap with a previous batch;
    processing each of said batches of time-series signals to obtain a PPG signal from each batch; and
    stitching together said PPG signal from each batch to form a continuous PPG signal, said stitching comprising using mid-point stitching.

2. The method of claim 1, wherein said video images are captured using a video imaging device capturing any combination of: NIR images, RGB images, RGB with NIR images, multispectral images, and hyperspectral video images.

3. The method of claim 1, wherein, in advance of obtaining said time-series signal, pre-processing said video to compensate for any of: a motion induced blur, an imaging blur, and slow illuminant variation.

4. The method of claim 1, further comprising:
    using said continuous PPG signal for detecting peak-to-peak pulse points in said continuous cardiac signal;
    analyzing said pulse points to obtain peak-to-peak pulse dynamics; and
    determining an occurrence of a cardiac arrhythmia based on said pulse dynamics.

5. The method of claim 1, wherein said PPG signal is filtered using a moving average comprising:

$$y(n) = \frac{1}{N} \sum_{1}^{N} x(n-i)$$

where N is the number of frames in a moving window of said video, x is an unfiltered PPG signal, y is a filtered PPG signal, n is a current frame and i is an index designating a moving frame.

6. The method of claim 1, wherein said video is captured over two imaging channels, further comprising using a constrained source separation algorithm with a reference signal that has a frequency range which approximates a frequency range of said subject's cardiac pulse.

7. The method of claim 4, wherein said peak-to-peak pulse points are detected in said continuous PPG signal using an adaptive threshold technique with successive thresholds being based on variations detected in previous magnitudes of said pulse peaks.

8. The method of claim 7, further comprising using a Poincare diagram of said peak-to-peak pulse dynamics, said Poincare diagram showing a relationship between consecutive beats.

9. The method of claim 7, further comprising normalizing said peak-to-peak pulse points to a frequency of 70 bpm to reduce pulse variations.

10. The method of claim 7, further comprising determining whether a time interval between consecutive peaks in said signal is outside an acceptable limit for said subject.

11. The method of claim 7, further comprising comparing said peak-to-peak pulse dynamics across different patients.

12. The method of claim 7, further comprising communicating said peak-to-peak pulse dynamics to a display device.

13. The method of claim 1, wherein said time-series signal comprises one of: stored values, and values generated from a streaming video.

14. A system for extracting photoplethysmographic (PPG) signals (i.e., cardiac signals) on a continuous basis from signals generated from batches of video images captured of a subject being monitored for cardiac function in a non-contact remote sensing environment, the system comprising:
    a memory; and
    a processor in communication with a memory, said processor executing machine readable instructions for performing:
    receiving a time-series signal generated from video images captured of a region of exposed skin where a photoplethysmographic (PPG) signal of a subject of interest can be registered;
    dividing said time-series signal into batches for processing, with successive batches having at least a 95% overlap with a previous batch;

processing each of said batches of time-series signals to obtain a PPG signal from each batch; and stitching together said PPG signal from each batch to form a continuous PPG signal, said stitching comprising using mid-point stitching.

15. The system of claim 14, wherein said video images are captured using a video imaging device capturing any combination of: NIR images, RGB images, RGB with NIR images, multispectral images, and hyperspectral video images.

16. The system of claim 14, wherein, in advance of obtaining said time-series signal, pre-processing said video to compensate for any of: a motion induced blur, an imaging blur, and slow illuminant variation.

17. The system of claim 14, further comprising:
using said continuous PPG signal for detecting peak-to-peak pulse points in said continuous cardiac signal;
analyzing said pulse points to obtain peak-to-peak pulse dynamics; and
determining an occurrence of a cardiac arrhythmia based on said pulse dynamics.

18. The system of claim 14, wherein said PPG signal is filtered using a moving average comprising:

$$y(n) = \frac{1}{N}\sum_{1}^{N} x(n-i)$$

where N is the number of frames in a moving window of said video, x is an unfiltered PPG signal, y is a filtered PPG signal, n is a current frame and i is an index designating a moving frame.

19. The system of claim 14, wherein said video is captured over two imaging channels, further comprising using a constrained source separation algorithm with a reference signal that has a frequency range which approximates a frequency range of said subject's cardiac pulse.

20. The system of claim 17, wherein said peak-to-peak pulse points are detected in said continuous PPG signal using an adaptive threshold technique with successive thresholds being based on variations detected in previous magnitudes of said pulse peaks.

21. The system of claim 20, further comprising using a Poincare diagram of said peak-to-peak pulse dynamics, said Poincare diagram showing a relationship between consecutive beats.

22. The system of claim 20, further comprising determining whether a time interval between consecutive peaks in said signal is outside an acceptable limit for said subject.

23. The system of claim 20, further comprising comparing said peak-to-peak pulse dynamics across different patients.

24. The system of claim 20, further comprising normalizing said peak-to-peak pulse points to a frequency of 70 bpm to reduce pulse variations.

25. The system of claim 14, wherein said time-series signal comprises one of: stored values, and values generated from a streaming video.

* * * * *